United States Patent
Law et al.

(10) Patent No.: US 7,857,137 B2
(45) Date of Patent: Dec. 28, 2010

(54) WOUND CARE KIT

(75) Inventors: Michael E. Law, Sparta, NJ (US); Kevin Hess, Mount Prospect, IL (US)

(73) Assignee: J&J Consumer Companies, Inc., Skillman, NJ (US)

(*) Notice: Subject to any disclaimer, the term of this patent is extended or adjusted under 35 U.S.C. 154(b) by 0 days.

(21) Appl. No.: 12/418,557

(22) Filed: Apr. 3, 2009

(65) Prior Publication Data

US 2010/0252472 A1  Oct. 7, 2010

(51) Int. Cl.
  *B65D 69/00* (2006.01)
  *A61B 19/02* (2006.01)
(52) U.S. Cl. .................... 206/570; 206/38; 206/441
(58) Field of Classification Search .......... 206/38–38.1, 206/440–441, 570–572, 803
  See application file for complete search history.

(56) References Cited

U.S. PATENT DOCUMENTS

| | | | | |
|---|---|---|---|---|
| 1,436,406 | A | * | 11/1922 | Schulz ................. 206/440 |
| 2,135,238 | A | * | 11/1938 | Malik ................... 206/803 |
| 2,159,904 | A | * | 5/1939 | McDonough .......... 206/440 |
| 2,276,766 | A | * | 3/1942 | De Witt ................ 206/440 |
| 2,377,117 | A | * | 5/1945 | Watkins ................ 206/38 |
| 2,391,301 | A | * | 12/1945 | Dukehart, Jr. ........ 206/441 |
| 3,091,378 | A | | 5/1963 | O'Dwyer |
| 3,227,867 | A | * | 1/1966 | Baker ................... 206/440 |
| 3,430,760 | A | | 3/1969 | Ulmer |
| 3,850,352 | A | | 11/1974 | Reiner |
| 4,299,344 | A | | 11/1981 | Yamashita et al. |
| 4,325,142 | A | | 4/1982 | Nakazawa |
| 4,598,027 | A | | 7/1986 | Johnson |
| 5,065,918 | A | | 11/1991 | Chun et al. |
| 5,232,136 | A | | 8/1993 | Unger |
| D351,280 | S | | 10/1994 | Pennington et al. |
| 5,388,741 | A | | 2/1995 | Hillinger |
| 5,755,367 | A | | 5/1998 | Yamada |
| D419,290 | S | | 1/2000 | Treyer et al. |
| 6,105,838 | A | | 8/2000 | Hansen |
| D471,005 | S | | 3/2003 | Hastings |
| 6,796,429 | B2 | * | 9/2004 | Cameron et al. ............ 206/440 |
| D575,157 | S | | 8/2008 | Jaketic |
| 2006/0289329 | A1 | * | 12/2006 | Miller ....................... 206/570 |
| 2007/0057004 | A1 | | 3/2007 | Butler et al. |
| 2008/0142403 | A1 | * | 6/2008 | Adler et al. ................ 206/570 |
| 2010/0059560 | A1 | * | 3/2010 | Lanum ...................... 206/571 |

OTHER PUBLICATIONS

Website: http://www.motivators.com/promotional-products-14html; May 12, 2008—(printout attached).

* cited by examiner

*Primary Examiner*—Bryon P Gehman
(74) *Attorney, Agent, or Firm*—Karen G. Horowitz

(57) ABSTRACT

A portable wound care kit sized, shaped, and configured to carry only articles necessary for wound care treatment. In one embodiment, the wound care kit contains only a container of wound treatment medicament and two or more wound coverings. However, the wound care kit may also be configured to carry wound cleansing wipes or wound wash. The wound care kit is configured to permit ready and easy access to the wound care treatment articles.

9 Claims, 3 Drawing Sheets

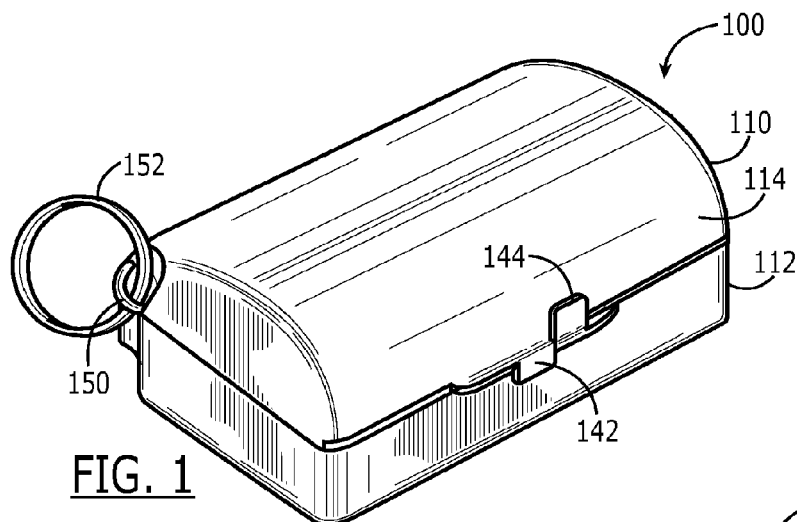
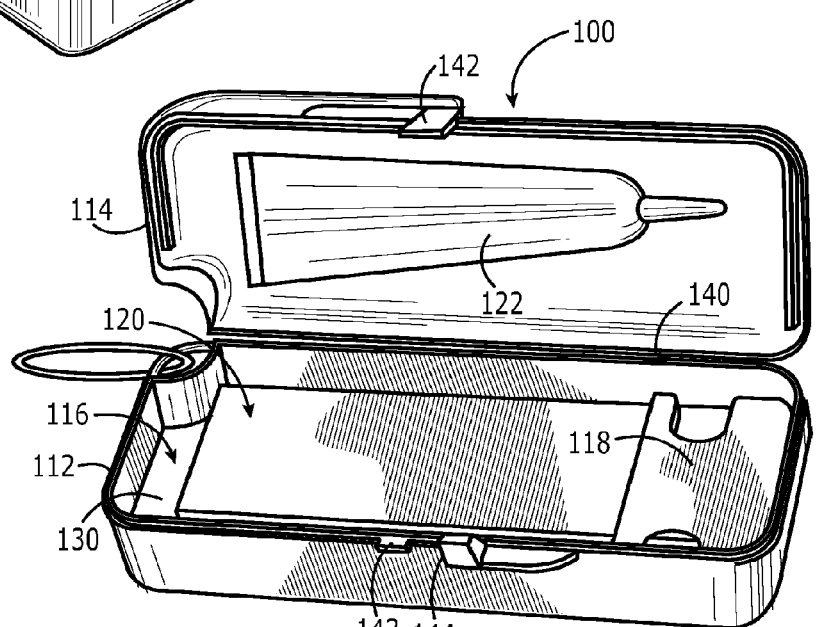
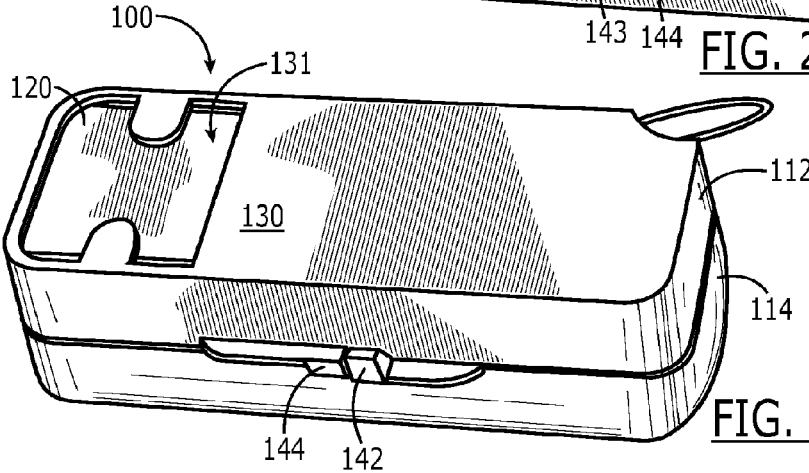

US 7,857,137 B2

WOUND CARE KIT

FIELD OF THE INVENTION

The present invention relates to portable wound care kits and more specifically to a portable wound care kit configured to carry a container of wound treatment medicament as well as wound coverings.

BACKGROUND OF THE INVENTION

First aid kits have been available for a number of years to provide a collection of supplies and equipment typically necessary or at least useful in giving first aid or for treating other generally minor medical conditions. Commercially-available first aid kits may range in size from wallet-sized through large-rucksack-sized. The housing of such kits may be formed from a relatively rigid material (such as a metal or rigid plastic case or box, or a wall-mounted cabinet) or a flexible pouch (made, for example, from a cloth or foam-type material). Such housings may have one or more chambers for holding the kit's contents. Various items may be provided in the first aid kit, depending on the purpose of the kit, who has assembled the kit, the desired size of the kit, etc.

Traditionally, kits available through consumer retail routes have been assembled for treatment of minor injuries only, and are commonly geared for placement in homes, work areas, schools, etc. Typical contents include a plurality of pain medication, gauze, alcohol-infused pads, tourniquets, adhesive bandages, wound treatment medicaments (e.g., an ointment, cream, powder, or liquid containing a wound-treating medicament such as an antibiotic or antiseptic or analgesic).

It is beneficial to have a first aid kit specifically for out-of-home activities. Such portable first aid kits need to be small if they are going to be carried by everyday people doing day-to-day chores by themselves, or with children. Often, portable first aid kits are carried in purses, tote bags, back packs, gym bags, etc., and if small enough, even on key chains or in clothing pockets. Often, the wound care kit is in the form of a container, which must be opened to find and pick out the contents. In today's fast-paced society, users desire fast and easy access to the contents of the first aid kit. In use, consumers who carry a portable first aid kit do not wish to be fumbling through the container of the kit to pull out the desired first aid items or find that the desired item is damaged (such as crushed, crumpled, or torn) because of the tight storage conditions. Also, since the kit may contain a plurality of items for multiple uses of the kit, the user may wish the kit to be formed for ready and easy removal of only one item at a time.

Because portability is so important for out-of-home use, the purpose of a portable first aid kits may be restricted to reduce the number of items to be carried by such kit. For instance, a portable first aid kit may be limited to wound care. Current first aid guidelines recommend the following regimen for treating a new wound: cleaning a wound, applying a wound treatment medicament such as one containing as an antibiotic, and covering the wound with a wound covering such as a bandage. It will be appreciated that whereas portable cases for adhesive bandages are known in the art, and portable cases for tubes of wound treatment medicament are also known in the art, there has as of yet not been a portable wound care kit providing both such items in a useful manner that permits ready access and use of such items. Therefore, there has been a long-felt need for a portable wound care kit that can both retain a plurality of wound coverings and a container of wound treatment medicament, as well as provide quick and easy access to these items.

SUMMARY OF THE INVENTION

In accordance with the principles of the present invention, a portable wound care kit is provided with a receptacle sized, shaped, and configured to contain or to carry one or more wound coverings, as well as a container of wound care treatment. More particularly, the kit preferably is configured to hold only wound care treatment articles, and preferably only necessary wound care treatment articles. Thus, the kit is as compact as possible. Moreover, the kit preferably permits reuse thereof. Accordingly, the wound coverings and wound care treatment may be replenished once the initial supply has been expended.

These and other features and advantages of the present invention will be readily apparent from the following detailed description of the invention, the scope of the invention being set out in the appended claims.

BRIEF DESCRIPTION OF THE DRAWINGS

FIG. 1 shows a perspective view of a first exemplary wound care kit formed in accordance with the principles of the present invention;

FIG. 2 shows the wound care kit of FIG. 1 in an open configuration;

FIG. 3 is a bottom perspective view of the wound care kit of FIG. 1, showing the manner in which wound coverings may be readily accessed;

DETAILED DESCRIPTION OF THE INVENTION

Figure 4:
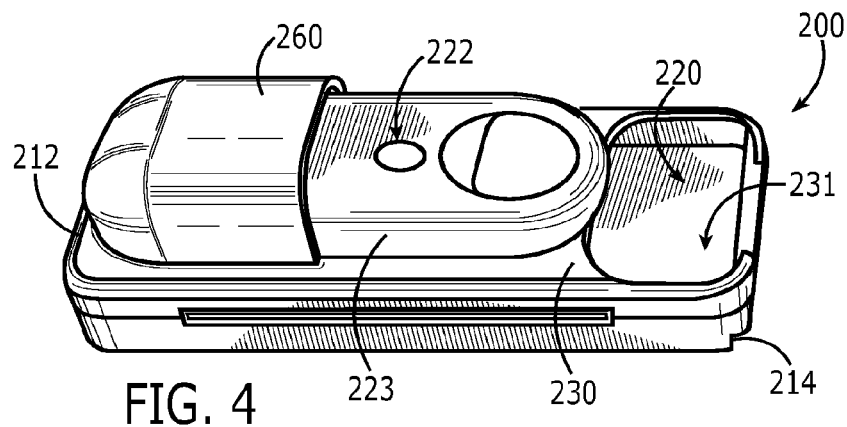
FIG. 4 shows a perspective view of a second exemplary wound care kit formed in accordance with the principles of the present invention.

In accordance with the principles of the present invention, a portable wound care kit is formed, shaped, and configured to house only items desired for the treatment of a wound, such as a cutaneous or superficial wound (e.g., a cut or scrape), and to facilitate easy and ready access to such items. For purposes of the present invention, as applicable to any of the disclosed embodiments as well as other embodiments falling within the scope of the present invention but not illustrated, the wound coverings may include adhesive bandages, gauze pads, or the like. Also for purposes of the present invention, as applicable to any of the disclosed embodiments as well as other embodiments falling within the scope of the present invention but not illustrated, the wound treatment medicament may be a container (such as, without limitation, a tube or jar or bottle or packet or spray dispenser or other type of container or dispenser) of cream, ointment, powder, or liquid containing an active ingredient known and accepted for treating wounds (such as an antibiotic, or an antiseptic).

Exemplary portable wound care kits formed in accordance with the principles of the present invention are illustrated in FIGS. 1-8. As will become better understood in the following detailed description of the invention, the principles of the present invention may be embodied in forms different from those illustrated in FIGS. 1-8 without departing from the spirit and scope of the present invention.

Turning now to the embodiment of FIGS. 1-3, exemplary portable wound care kit 100 has a housing 110 in the form of a relatively rigid case having a main body 112 and a lid 114. Main body 112 is configured to have an interior 116 configured to receive, hold, and maintain the desired items for wound care, namely, one or more wound coverings 120 and a wound treatment medicament 122 (illustrated as a tube, but which may be in the form of a stick, spray dispenser, bottle, jar, foil packet, etc., instead). It will be appreciated that main body interior 116 preferably is sized and shaped to substantially match the size and shape of a typical adhesive bandage (e.g., ¾ inch×3 inch or ⅝ inch by 2¼ inch) to reduce shifting of adhesive bandages therein as well as to permit sufficient space so that the adhesive bandages need not be bent or otherwise deformed to fit within main body interior 116. Of course, it will be appreciated that it may be desirable to reduce the overall size of housing 110 to less than the typical length of an adhesive bandage. In such case, adhesive bandages to be held within the housing of a wound care kit formed in accordance with the principles of the present invention may be rolled or otherwise folded in a manner that does not impair the function or appearance (which may be very important to young children) of the adhesive bandage when removed from the wound care kit. In addition, main body interior 116 functions as a holder for a container of wound treatment medicament and thus preferably is sized and shaped to receive or house a container of wound treatment medicament, most preferably in a manner that reduces if not eliminates any adverse physical interactions between the adhesive bandages and wound treatment medicament to be housed within main body interior 116.

A retaining element 118, such as a partial wall, may be provided to maintain one or more (preferably at least two or more) adhesive bandages 120 in place within main body interior 116. Such retaining element is beneficial in maintaining order within main body interior 116, which may reduce any damage that may result from shifting of bandages 120 (particularly relative to wound treatment medicament 122) if not held in a predetermined place within main body interior 116. In addition, retaining element 118 is spaced above bottom wall 130 of main body 112, and bottom wall 130 may be a partial wall with a cut-away region 131 in the vicinity of retaining element 118. It will be appreciated that adhesive bandages 120 are accessible from the back side of bottom wall 130 (illustrated in FIG. 3) via cut-away region 131. Retaining element 118 facilitates dispensation of adhesive bandages 120 through cut-away region 131 by maintaining adhesive bandages 120 in place at such region for ready dispensation.

Lid 114 of wound care kit housing 110 is illustrated in the embodiment of FIGS. 1-3 as domed to provide housing interior 116 with sufficient volume to contain wound treatment medicament 122. Of course, other exterior shapes of the top side of housing 110 (and thus the top of lid 114, as illustrated in FIG. 1) are within the scope of the present invention. Preferably, lid 114 is readily separable from main body 112 to permit easy and ready access to wound treatment medicament 116, as well as to permit refilling of wound care kit 100. In the exemplary embodiment of FIGS. 1-3, lid 114 is hingedly coupled to main body 112, such as by a living hinge 140 (which hinge simplifies manufacturing and assembly of housing 110, as well as wound care kit 100). Any type of mechanism known in the art may be used to maintain lid 114 in a closed configuration. For instance, one or more latches or pry tabs may be provided to catch on one or more detents. As illustrated in FIGS. 1 and 2, latch 142 may be provided on lid 114 to catch on detent 143 on main body 112. Latch 144 may be provided on main body 112 to facilitate opening of lid 114 by engagement of latch 144 in conjunction with latch 142. It will be appreciated that latch 144 need not also catch on a detent (which, if provided, would be provided on lid 114), and may simply be provided for symmetry and/or for facilitation of opening of lid 114 when engaging latch 142. It will be appreciated that other manners of maintaining lid 114 in a closed configuration with respect to main body 112 (such as mating pins and bosses) are within the scope of the present invention.

In accordance with the principles of the present invention, wound care kit housing 110 preferably is shaped for ready portability. Wound care kit may be stored in a relatively compact place, such as a handbag or backpack. If wound care kit is not to be stored in a substantially enclosed item, a connection element may be provided to couple wound care kit 100 to another article, such as for carrying with another article or outside a larger article. For instance, wound care kit 100 may be provided with a ring 150 (preferably integrally formed with main body 112 or lid 114 of housing 110) through which a key ring 152 or other connection element (e.g., a lanyard, chain, clip, or other connection element known in the art) may be coupled. The connection element may be configured for connection to any desired article such as keys, a belt hook, a back pack handle, a zipper pull or another article.

It will be appreciated that main body interior 116 provides a convenient enclosed receptacle or storage area for a container for wound care medicament. Enclosure of the container of wound treatment medicament is particularly desirable if the container is not rigid or otherwise relatively resistant to damage. However, if wound care medicament is provided in a relatively rigid container, it may be desirable to reduce the size of a wound care kit formed in accordance with the principles of the present invention by simply providing a holder for the wound care medicament on the outside of the wound care kit housing. Exemplary wound care kits formed in accordance with the principles of the present invention to hold or to carry a wound treatment medicament on the exterior of the housing of the kit are illustrated in FIGS. 4-8.

Figure 5:
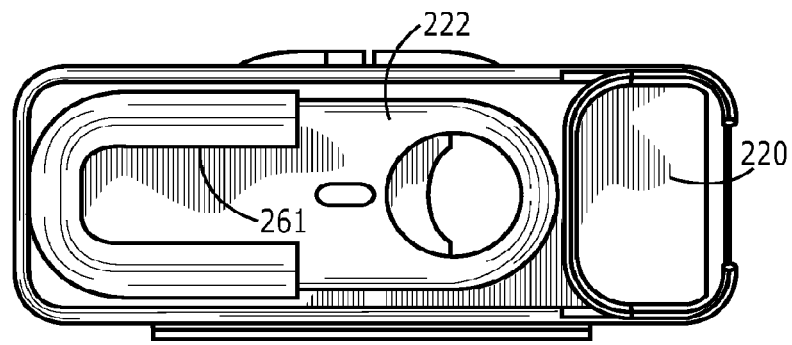
FIG. 5 shows a modification that may be made to the wound care kit of FIG. 4.
Figure 6:
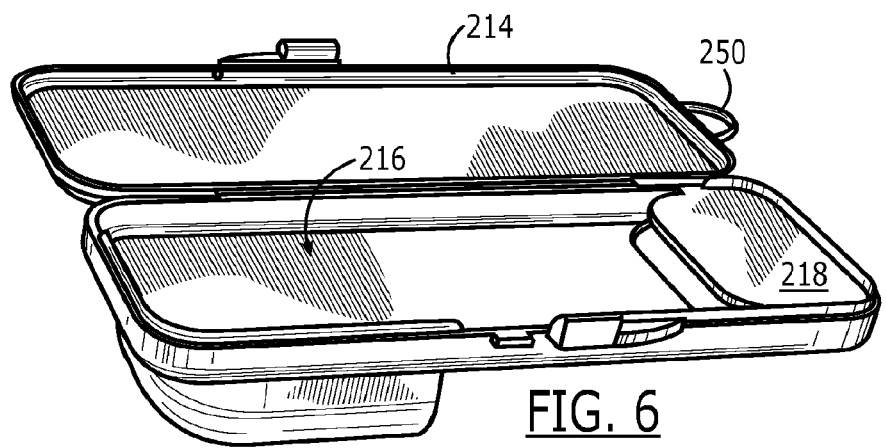
FIG. 6 shows the wound care kit of FIG. 4 in an open configuration.
Figure 7:
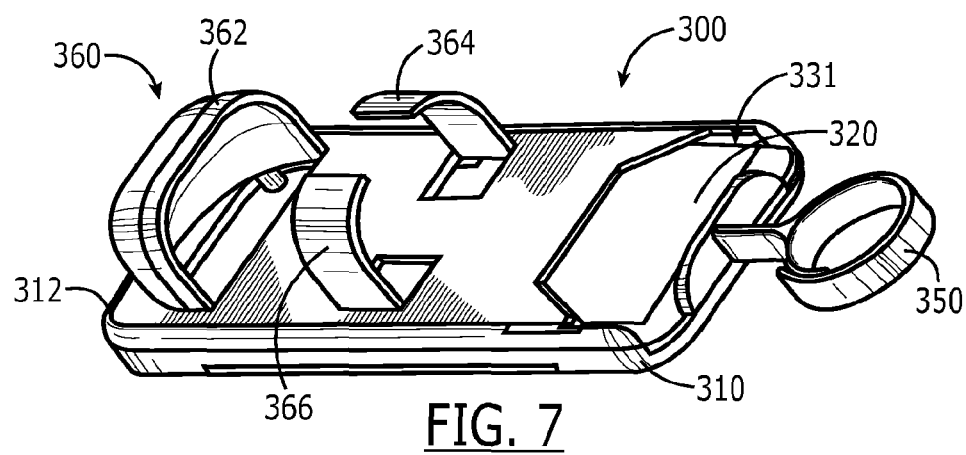
FIG. 7 is a perspective view of a third exemplary wound care kit formed in accordance with the principles of the present invention.
Figure 8:
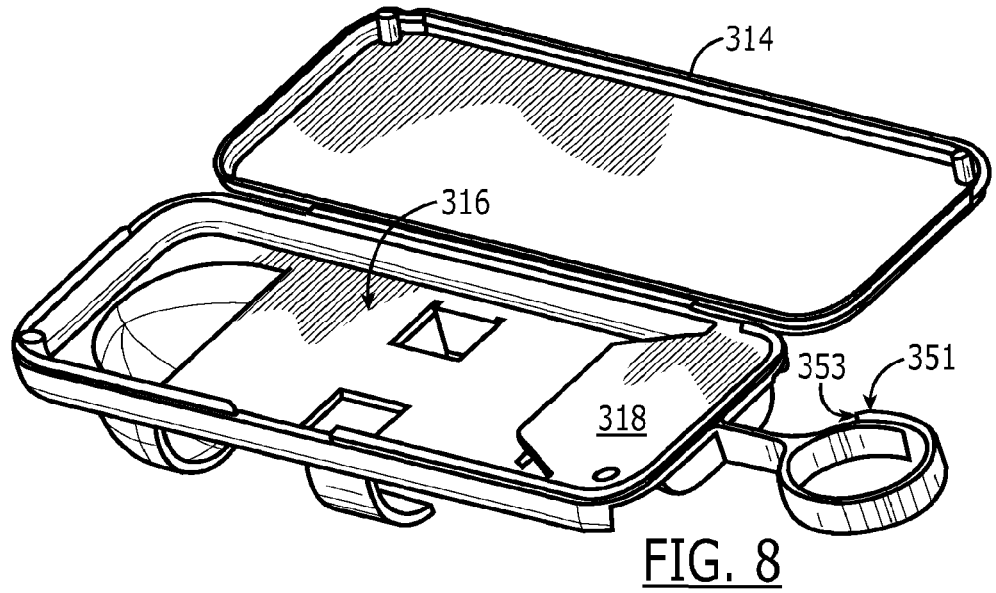
FIG. 8 shows the wound care kit of FIG. 7 in an open configuration.

Exemplary wound care kit 200, illustrated in FIGS. 4-6, and exemplary wound care kit 300, illustrated in FIGS. 7 and 8, provide the same beneficial features of exemplary wound care kit 100 provided in accordance with the principles of the present. Namely, exemplary wound care kits 200 and 300 carry or contain one or more (preferably two or more) wound coverings 220, 320 and a container of wound treatment medicament 222 (not illustrated in the embodiment of FIGS. 7 and 8, though a similar or the same wound treatment medicament 222 may be used in the embodiment of FIGS. 7 and 8 as illustrated in the embodiments of FIGS. 4 and 5) in a convenient manner that permits ready access and use of both wound treatment articles. However, unlike wound care kit 100, wound care kits 200 and 300 carry a wound treatment medicament container on an exterior of their respective housings 210, 310, as will be described in further detail below. For the sake of convenience, elements of wound care kit 200 similar to elements of wound care kit 100 are labeled with the same reference number increased by 100, and elements of wound care kit 300 similar to elements of wound care kit 100 are labeled with the same reference number increased by 200.

Exemplary wound care kits 200 and 300 are sized, shaped, and configured to carry a wound treatment medicament contained or carried in a spray dispenser (such as a spray dispenser disclosed in co-pending U.S. patent application Ser.

Nos. 11/142,940 and 11/143,976, both filed on Jun. 2, 2005, which applications are hereby incorporated by reference herein in their entireties). Accordingly, wound treatment medicament container 223 is relatively rigid and does not need to be enclosed in a more rigid housing (as generally is the case with a wound treatment medicament contained or carried in a tube, such as the wound treatment medicament illustrated in FIG. 2). As such, main body 212 of wound care kit housing 210 is provided with a holder 260 and main body 312 of wound care kit housing 310 is provided with a holder 360, both of which holders 260, 360 being configured to hold a wound treatment medicament container 223 securely so that container 223 is maintained in holder 260, 360 when wound care kit 200, 300 is stowed in even a small space (such as a handbag containing various other items). Holders 260 and 360 further are configured to permit relatively easy removal of wound treatment medicament container 223 therefrom, such as by sliding with respect to housing 210 or 310 with average manual force exerted by an adult. For instance, holder 260 may be configured to provide a friction fit with container 223 inserted therein. If desired, a cut-out 261 may be provided in holder 260 to facilitate access to container 223 for pushing or sliding container 223 relative to housing 210. Bottom portion 362 of holder 360 on wound care kit housing 310 is similar to holder 260, except less material is used to form bottom portion 362 than to form holder 260. Accordingly, holder 360 is further provided with clamping elements 364 and 366 sized, shaped, and configured to secure clamp a wound treatment medicament container in place on housing 310. As such, bottom portion 362 of holder 360 need not be configured to provide a friction fit with the wound treatment medicament container, but, instead, may simply function to prevent slippage of the wound treatment medicament container with respect to housing 310. It will be appreciated that although wound treatment medicament container 223 is shorter than housing 210 (allowing wound coverings 220 to be accessed while wound treatment medicament container 223 is held within holder 260) and thus cannot be activated to dispense wound treatment medicament while stored, housing 210 may be modified to permit dispensing of wound treatment medicament while held within holder 260.

Similar to wound care kit 100, respective housings 210 and 310 of wound care kits 300 and 400 have an interior 216, 316, respectively forming a receptacle or storage area for containing a supply of adhesive bandages 220, 320. A cut-away 231 is provided in wall 230 of housing main body 212 to permit access to and removal of an adhesive bandage 220. Likewise, cut-away 331 is provided in wall 330 of housing main body 312 to permit access to and removal of an adhesive bandage 320. To facilitate replenishment of the adhesive bandage supply contained in wound care kits 200, 300, housings 210, 310 may be provided with a lid 214, 314 similar to that described with respect to housing 110 of wound care kit 100, as illustrated in FIGS. 6 and 8. Also similar to wound care kit 100, a retaining element 218, 318, such as a partial wall, may be provided to maintain one or more (preferably at least two or more) adhesive bandages 220, 320 in place within main body interior 216, 316. However, it will be appreciated that to simplify the design of housing 210, 310, a lid movable with respect to main body to provide open access to housing interior 216, 316 may not be necessary. Interior 216, 316 may be accessible via the cut-away region 231, 331 through which adhesive bandages 220, 320 are removed so that adhesive bandages 220, 320 may be replenished through the same access opening through which they are removed.

A ring or loop 250 may be formed on housing 210 of wound care kit 200 to provide similar benefits provided by ring or loop 150 on housing 110 of wound care kit 100. In the embodiment of FIGS. 7 and 8, instead of a ring or loop, a connecting loop 351 may be provided with a free end 353 selectively separable from the rest of connecting loop 351 to permit insertion of free end 353 through an article for retention of the article on connecting loop 351 once free end 353 springs back into engagement with the rest of connecting loop 351.

Because a compact design is highly desirable, the number of wound care items contained in a wound care kit formed in accordance with the principles of the present invention preferably is limited to the essential elements. Although the wound care kits described herein are described as containing just wound treatment medicaments and wound coverings, it will be appreciated that modifications within ordinary skill of the art may be made to house, and preferably also to facilitate dispensation of, wound cleansing wipes or wound wash. This may be particularly desirable in view of the commonly-accepted wound treatment regimen which recommends cleaning a wound before applying a wound treatment medicament and before covering the wound. Wound cleansing wipes may be contained in any desired container, such as, without limitation, a tube or in individual packets. Similarly, a wound wash may be provided in any type of container such as, without limitation, a bottle, jar, or spray dispenser.

It will be appreciated features described with respect to one embodiment typically may be applied to another embodiment, whether or not explicitly indicated. The various features described herein may be used singly or in any combination thereof. Therefore, the present invention is not limited to only the embodiments specifically described herein, but extends to variations that provide the basic elements of the present invention, namely, convenient portable maintenance of a wound treatment medicament and wound coverings together and in easy reach. Preferably, though not necessarily, a wound care kit formed in accordance with the principles of the present invention is refillable and thus reusable.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. For instance, additional features may be provided that do not detract from the basic principles of the present invention, such as the provision of a magnet on an exterior of the wound care kit housing to permit attachment of the housing to another magnetic object. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. For example, elements shown as integrally formed may be constructed of multiple parts or elements shown as multiple parts may be integrally formed, the operation of elements may be reversed or otherwise varied, the size or dimensions of the elements may be varied. The presently disclosed embodiments are therefore to be considered in all respects as illustrative and not restrictive, the scope of the invention being indicated by the appended claims, and not limited to the foregoing description.

What is claimed is:

1. A compact portable wound care kit comprising:
a container of wound treatment medicament;
two or more wound coverings; and
a housing having:
- a main body having a plurality of outer walls and an interior defined by said outer walls of said main body, said main body interior being sized, shaped, and configured to retain said two or more wound coverings therein, and sized and shaped at its perimeter to substantially match the size and shape of the perimeter of an individual one of said wound coverings to reduce shifting of said wound coverings therein;
- a lid coupled to said main body to enclose said main body interior when in a closed position and to access said main body interior when in an opened position; and
- an access opening formed in a said outer wall of said main body permit withdrawal of one wound covering therethrough without opening said lid; and wherein: said housing has a longer side defining a housing length and a shorter side defining a housing width, and is sized and shaped to hold said wound treatment medicament container and wound coverings in parallel and side-by-side along said housing length, said wound treatment medicament container and said wound coverings being shorter than said housing length and narrower than said housing width.

2. A compact portable wound care kit as in claim 1, wherein said wound coverings and said container of wound treatment medicament are held together within said housing.

3. A compact portable wound care kit as in claim 2, wherein a retaining element is provided in said main body interior to retain said two or more wound coverings in a predetermined place in said main body interior with respect to said access opening.

4. A portable wound care kit as in claim 1, wherein a holder is formed on an exterior of said main body, and is sized, shaped and configured to engage and to hold a wound treatment medicament container securely on said housing to permit access to said wound treatment medicament container from the exterior of said housing.

5. A portable wound care kit as in claim 4, wherein said access opening and said wound treatment medicament container holder are formed on the same side of said housing.

6. A compact portable wound care kit as in claim 1, wherein said wound treatment medicament container is selected from the group consisting of: a tube, a bottle, a jar, two or more packets, a stick, and a spray dispenser.

7. A compact portable wound care kit as in claim 1, wherein said housing further comprises a holder sized, shaped, and configured to hold said container of wound treatment medicament therein.

8. A compact portable wound care kit as in claim 1, wherein said lid is coupled to said main body along said housing length to permit access to said main body interior along said housing length to lay said wound coverings flat within said main body interior.

9. A compact portable wound care kit as in claim 1, wherein:
said wound coverings are laid flat within said main body interior and said container of wound treatment medicament is laid against said wound coverings within said main body interior; and
said main body interior has a length corresponding to the greater of the individual lengths of said wound coverings and said container of wound treatment medicament.

* * * * *

UNITED STATES PATENT AND TRADEMARK OFFICE
CERTIFICATE OF CORRECTION

PATENT NO. : 7,857,137 B2  
APPLICATION NO. : 12/418557  
DATED : December 28, 2010  
INVENTOR(S) : Michael E. Law and Kevin Hess It is certified that error appears in the above-identified patent and that said Letters Patent is hereby corrected as shown below:

Claim 8, col. 8, Ln 24-25, delete: "to lay said wound coverings flat within said main body interior."

Signed and Sealed this  
First Day of May, 2012

David J. Kappos  
*Director of the United States Patent and Trademark Office*